US007816358B2

(12) United States Patent
Uragg et al.

(10) Patent No.: US 7,816,358 B2
(45) Date of Patent: *Oct. 19, 2010

(54) PHARMACEUTICAL FORMULATIONS COMPRISING N,N'-DISUBSTITUTED PIPERAZINE COMPOUNDS

(75) Inventors: Heinz Uragg, Stolberg (DE); Corinna Maul, Aachen (DE); Helmut Buschmann, Esplugues de Llobregat (DE); Bernd Sundermann, Aachen (DE); Michael Haubrand, Aachen (DE); Boris Chizh, Whittlesford (GB)

(73) Assignee: Gruenenthal GmbH, Aauchen (DE)

( * ) Notice: Subject to any disclaimer, the term of this patent is extended or adjusted under 35 U.S.C. 154(b) by 1820 days.

This patent is subject to a terminal disclaimer.

(21) Appl. No.: 10/866,100

(22) Filed: Jun. 14, 2004

(65) Prior Publication Data

US 2005/0038034 A1    Feb. 17, 2005

Related U.S. Application Data

(63) Continuation of application No. PCT/EP02/13911, filed on Dec. 9, 2002.

(30) Foreign Application Priority Data

Dec. 14, 2001  (DE) ............................. 101 61 809

(51) Int. Cl.
*A61K 31/497* (2006.01)
*C07D 241/04* (2006.01)
(52) U.S. Cl. .................................. 514/252.12; 544/358
(58) Field of Classification Search ............ 514/252.12; 544/358
See application file for complete search history.

(56) References Cited

U.S. PATENT DOCUMENTS

| 3,716,538 A * | 2/1973 | Schut ........................ 544/392 |
| 4,203,986 A | 5/1980 | Joullie et al. |
| 7,030,276 B2 | 4/2006 | Finkam et al. |
| 2003/0008859 A1 | 1/2003 | Sundermann et al. |

FOREIGN PATENT DOCUMENTS

DE   19963175   7/2001

WO   WO03/051855 *  6/2003
WO   WO 2004/020390 A1   3/2004

OTHER PUBLICATIONS

Mukaiyama 'From a synthetic organic chemist' Pure and Applied Chemistry, 69(2), p. 257-258, 1997.*
Chiang et al 'Intraocular Pressure Lower Effects of Novel Arylpiperazine Derivatives' Journal of Ocular Pharmacology, 14(4), p. 313-322, 1998.*
Patani et al 'Bioisosterism: A rational approach in drug design' Chemistry Reviews, vol. 96, p. 3147-3176, 1996.*
Cannon, J.G., Chapter Nineteen in Burger's Medicinal Chemistry and Drug Discovery Volume I: Principles and Practice Wiley Interscience, Fifth Edition, p. 783-802 and 784, 1995.*
Horig et al, "From Bench to clinic and back: Perspective on the 1st IQPC Tranlational Research conference" Journal of Translational Medicine, 2(44), p. 1-8, 2004.*
Schafer et al 'Failure is an option: learning from unsuccessful proof-of-concept trials' Drug Discovery Today, 13(21/22), p. 913-916, 2008.*
Justin S. Bryans et al., "3-Substituted GABA Analogs with Central Nervous System Activity: A Review", Med. Res. Rev., 1999, pp. 149-177, 19, John Wiley & Sons, Inc.
Mark Schrope, "The Coxsackie Kicker", News in Brief, Modern Drug Discovery, Sep. 2000, p. 11, 2000 American Chemical Society.
Albert Lespagnol et al., "Chemical and Pharmacodynamic Study of Benzylacetophenone Derivatives", 1972, p. 293-239, Lab Pharmacodyn, Chim. Ther., France.
Milka Nikolova et al., "Synthesis and Pharmacological Screening of a Group of Piperazine Derivatives Analgesic Activity", IL Farmaco, 1993, pp. 459-472, 48, 4, XP-000617338.
Masahisa Hashimoto et al., "Metabolism of a New Analgesic Agent, *di-erythro*-1-Phenyl-2-(o-Chlorophenyl)-2-[4-(*p*-Methoxybenzyl)-1-Piperazinyl]Ethanol Dihydrochloride, in Rats", Drug Metabolism and Disposition, 1979, pp. 435-441, vol. 7, No. 6, The American Society of Pharmacology and Experiential Therapeutics, USA, XP-973712A.
Jean C. Cazin et al., "Pharmacological Activity of Aminoalcohols Derivated from Benzylacetophenone", Eur. J. Med. Chem.—Chim. Ther., 1974, pp. 408-415, 9, 4, France.
M. Boniface, "Computer Calculation of Effective Dose Using the Method of Probits", 1972, Abstract, Bull. Soc. Pharm., 4, France.

* cited by examiner

*Primary Examiner*—Brandon J Fetterolf
*Assistant Examiner*—Christopher R Stone
(74) *Attorney, Agent, or Firm*—Crowell & Moring LLP

(57) ABSTRACT

Pharmaceutical formulations comprising N,N'disubstituted piperazine compounds and related methods of treatment using these formulations.

15 Claims, No Drawings

PHARMACEUTICAL FORMULATIONS COMPRISING N,N'-DISUBSTITUTED PIPERAZINE COMPOUNDS

CROSS-REFERENCE TO RELATED APPLICATIONS

This application is a continuation of International Patent Application No. PCT/EP02/13911, filed Dec. 9, 2002, designating the United States of America, and published in German as WO 03/051369 A1, the entire disclosure of which is incorporated herein by reference. Priority is claimed based on Federal Republic of Germany Patent Application No. DE 101 61 809.3, filed Dec. 14, 2001.

FIELD OF THE INVENTION

The present invention relates to pharmaceutical formulations comprising N,N'-disubstituted piperazine compounds and to the use of these compounds for the preparation of pharmaceutical formulations and in related treatment methods.

BACKGROUND OF THE INVENTION

Treatment of pain is of great importance in medicine. There is a worldwide need for active pain therapies. The urgent need for action for target-orientated treatment of chronic and non-chronic states of pain appropriate for the patient, meaning successful and satisfactory pain treatment for the patient, is documented in the large number of scientific works which have recently been published in the field of applied analgesia and fundamental research on nociception. Treatment of epilepsy is also of great importance in medicine.

The cyclic GABA analog gabapentin is a clinically tested antiepileptic having an anticonvulsive action. Gabapentin moreover shows further interesting and medically relevant properties, in particular as an analgesic. Gabapentin is also prescribed for migraine and bipolar disorders as well as hot flashes (e.g. in the postmenopause) by doctors performing treatment (M. Schrope, Modern Drug Discovery, September 2000, p. 11). Other indications in which gabapentin shows a therapeutic potential have been identified during human studies and in clinical use (J. S. Bryans, D. J. Wustrow; "3-Substituted GABA Analogs with Central Nervous System Activity: A Review" in Med. Res. Rev. (1999), p. 149-177). The action of gabapentin is listed in detail in this review article. Thus, gabapentin is active in the treatment of chronic pain and behavioral disturbances. There are listed in particular: anticonvulsives and antiepileptic actions, use against chronic, neuropathic pain, in particular thermal hyperalgesia, mechanical allodynia and cold allodynia. It furthermore acts successfully against neuropathy caused by nerve damage, in particular precisely neuropathic pain, and also inflammatory and postoperative pain. Gabapentin is also successful with antipsychotic effects, in particular as an anxiolytic. Further indications which have been investigated include: amyotrophic lateral sclerosis (ALS), reflex sympathetic dystrophy (RSD), spastic paralysis, restless leg syndrome, treatment of symptoms and pain caused by multiple sclerosis, acquired nystagmus and treatment of the symptoms of Parkinson's disease, of painful diabetic neuropathy and of psychiatric disorders, e.g. bipolar disorders, mood swings and manic behaviour. The use of gabapentin was also successful on erythromelalgic pain, postpoliomyelitis pain, trigeminal neuralgia and postherpetic neuralgia (Bryans and Wustrow (1999), loc. cit.). The general activity in neurodegenerative diseases is generally known and can also be seen from the review article mentioned, with the aid of the examples. Such neurodegenerative diseases are e.g. Alzheimer's disease, Huntington's disease, Parkinson's disease and epilepsy. The activity of gabapentin on gastrointestinal damage is also known.

SUMMARY OF THE INVENTION

One object of the invention is to provide new pharmaceutical formulations which correspond to gabapentin in their action and preferably have an analgesic and/or antiepileptic action.

According to the invention, this object is achieved by providing pharmaceutical formulations comprising N,N'-disubstituted piperazine compounds of the formula I given below, since these pharmaceutical formulations in particular have a pronounced analgesic action and a pronounced action against epilepsy and can be employed for treatment of pain, in particular neuropathic, chronic and/or acute pain, for treatment of symptoms associated in particular with neuropathic pain, and/or other related indications, for treatment of migraine, hyperalgesia and/or allodynia, in particular thermal hyperalgesia, mechanical hyperalgesia, mechanical allodynia and/or cold allodynia, for treatment of inflammatory and/or postoperative pain, for treatment of neurodegenerative diseases, such as Alzheimer's disease, Huntington's disease, Parkinson's disease and/or epilepsy, for treatment of psychiatric and/or neuropathological disorders, such as bipolar disorders, anxiety, panic attacks, mood swings, manic behaviour, depressions and manic-depressive behaviour, for treatment of hot flashes, symptoms in the postmenopause, amyotrophic lateral sclerosis (ALS), reflex sympathetic dystrophy (RSD), spastic paralysis, restless leg syndrome, acquired nystagmus and painful diabetic neuropathy, for treatment of symptoms and/or pain caused by multiple sclerosis and/or Parkinson's disease, and for treatment of gastrointestinal damage, erythromelalgic and/or postpoliomyelitic pain and trigeminal and/or postherpetic neuralgia.

The present invention therefore provides pharmaceutical formulations comprising at least one N,N'-disubstituted piperazine compound corresponding to formula I

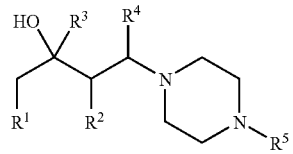

wherein $R^1$ and $R^2$ are identical or different and in each case represent a linear or branched, saturated or unsaturated aliphatic radical, or together form a $(CH_2)_n$ chain, wherein n represents an integer, $R^3$ and $R^5$ are identical or different and in each case represent a linear or branched, saturated or unsaturated aliphatic radical, a saturated or unsaturated cycloaliphatic radical, an aryl radical or a heteroaryl radical, wherein the particular ring system optionally can be mono- or polysubstituted and/or can be bonded via a linear or branched, saturated or unsaturated aliphatic bridge and/or the aryl or heteroaryl radical can be part of a polycyclic system, $R^4$ represents hydrogen or an optionally mono- or polysubstituted aryl or heteroaryl radical, wherein the aryl or heteroaryl radical can be part of a polycyclic system, in the form of its diastereomers, its enantiomers and mixtures thereof—including its racemates—and in the form of corresponding bases, salts and solvates, as the active compound and optionally physiologically acceptable auxiliary substances.

Pharmaceutical formulations comprising at least one compound corresponding to formula I wherein $R^1$ and $R^2$ are identical or different and in each case represent a linear or branched, saturated or unsaturated aliphatic $C_{1-6}$ radical or together form a $(CH_2)_n$ chain, wherein n represents an integer from 2 to 9.

$R^3$ represents a linear or branched, saturated or unsaturated aliphatic $C_{1-6}$ radical, a saturated or unsaturated cycloaliphatic $C_{3-7}$ radical, a phenyl radical or a five- or six-membered heteroaryl radical, wherein the particular ring system optionally can be mono- or polysubstituted and/or can be bonded via a linear or branched, saturated or unsaturated aliphatic $C_{1-5}$ bridge, $R_4$ represents hydrogen or a phenyl radical, and $R^5$ represents a linear or branched, saturated or unsaturated aliphatic $C_{1-6}$ radical or an optionally substituted phenyl radical, are preferred.

Pharmaceutical formulations comprising at least one compound corresponding to formula I wherein $R^1$ and $R^2$ are identical or different and in each case represent a linear or branched, saturated or unsaturated aliphatic $C_{1-3}$ radical or together form a $(CH_2)_n$ chain, wherein n represents an integer from 2 to 9, $R^3$ represents a linear or branched, saturated or unsaturated aliphatic $C_{1-3}$ radical, a saturated or unsaturated cycloaliphatic $C_{5-6}$ radical, a phenyl radical or a five- or six-membered heteroaryl radical, wherein the particular ring system optionally can be mono- or polysubstituted by halogen, an alkyl group, an alkoxy group and/or a trihalogenated alkyl group and/or can be bonded via a linear or branched, saturated or unsaturated aliphatic $C_{1-3}$ bridge, $R^4$ represents hydrogen or a phenyl radical, and $R^5$ represents a linear or branched, saturated or unsaturated aliphatic $C_{1-3}$ radical or a phenyl radical which is optionally substituted by halogen or an alkoxy group, are furthermore preferred.

Pharmaceutical formulations comprising at least one compound corresponding to formula 1 wherein $R^1$ and $R^2$ in each case represent a methyl group or together form a $(CH_2)_n$ chain, wherein n represents 3, 4, 5 or 9, $R^3$ represents a vinyl radical, a cyclopentyl radical, a cyclohexyl radical, a thiophenyl radical or a phenyl radical, wherein the cyclohexyl radical optionally can be bonded via a methylene bridge or the phenyl radical optionally can be mono- or polysubstituted by fluorine, chlorine, a methyl group, an isopropyl group, a methoxy group and/or a trifluoromethyl group and/or optionally can be bonded via a linear, saturated aliphatic $C_{1-3}$ bridge or an ethynyl bridge, $R^4$ represents hydrogen or a phenyl radical, and $R^5$ represents a methyl group or a phenyl radical which is optionally substituted by chlorine or a methoxy group are furthermore preferred.

Pharmaceutical formulations comprising at least one compound corresponding to formula II

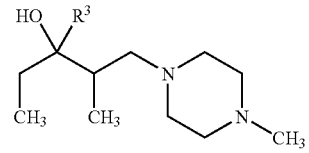

wherein $R^3$ represents a linear or branched, saturated or unsaturated aliphatic radical, a saturated or unsaturated cycloaliphatic radical, an aryl radical or a heteroaryl radical, wherein the particular ring system optionally can be mono- or polysubstituted and/or can be bonded via a linear or branched, saturated or unsaturated aliphatic bridge and/or the aryl or heteroaryl radical can be part of a polycyclic system, are particularly preferred.

Pharmaceutical formulations comprising at least one compound corresponding to formula III

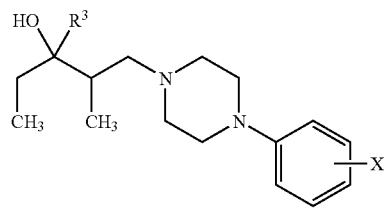

wherein

X represents hydrogen, halogen or an alkoxy group, preferably hydrogen, chlorine or a methoxy group, and $R^3$ represents a linear or branched, saturated or unsaturated aliphatic radical, a saturated or unsaturated cycloaliphatic radical, an aryl radical or a heteroaryl radical, wherein the particular ring system optionally can be mono- or polysubstituted and/or can be bonded via a linear or branched, saturated or unsaturated aliphatic bridge and/or the aryl or heteroaryl radical can be part of a polycyclic system, are particularly preferred.

Pharmaceutical formulations comprising at least one compound corresponding to formula IV

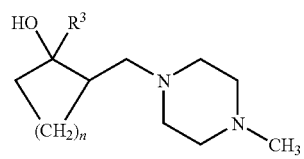

wherein n represents an integer from 2 to 9 and

R³ represents a linear or branched, saturated or unsaturated aliphatic radical, a saturated or unsaturated cycloaliphatic radical, an aryl radical or a heteroaryl radical, wherein the particular ring system optionally can be mono- or polysubstituted and/or can be bonded via a linear or branched, saturated or unsaturated aliphatic bridge and/or the aryl or heteroaryl radical can be part of a polycyclic system, are particularly preferred.

Pharmaceutical formulations comprising at least one compound corresponding to formula V

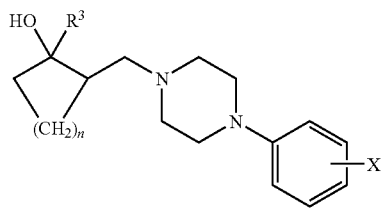

V wherein n represents an integer from 2 to 9,

X represents hydrogen, halogen or an alkoxy group, preferably hydrogen, chlorine or a methoxy group, and R³ represents a linear or branched, saturated or unsaturated aliphatic radical, a saturated or unsaturated cycloaliphatic radical, an aryl radical or a heteroaryl radical, wherein the particular ring system optionally can be mono- or polysubstituted and/or can be bonded via a linear or branched, saturated or unsaturated aliphatic bridge and/or the aryl or heteroaryl radical can be part of a polycyclic system, are particularly preferred.

Pharmaceutical formulations comprising at least one compound corresponding to formula VI

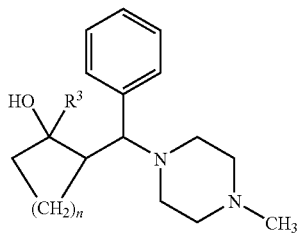

VI wherein n represents an integer from 2 to 9 and

R³ represents a linear or branched, saturated or unsaturated aliphatic radical, a saturated or unsaturated cycloaliphatic radical, an aryl radical or a heteroaryl radical, wherein the particular ring system optionally can be mono- or polysubstituted and/or can be bonded via a linear or branched, saturated or unsaturated aliphatic bridge and/or the aryl or heteroaryl radical can be part of a polycyclic system, are particularly preferred.

Pharmaceutical formulations comprising at least one compound corresponding to formula VII

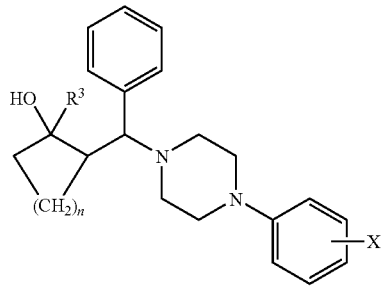

VII wherein n represents an integer from 2 to 9,

X represents hydrogen, halogen or an alkoxy group, preferably hydrogen, chlorine or a methoxy group, and R³ represents a linear or branched, saturated or unsaturated aliphatic radical, a saturated or unsaturated cycloaliphatic radical, an aryl radical or a heteroaryl radical, wherein the particular ring system optionally can be mono- or polysubstituted and/or can be bonded via a linear or branched, saturated or unsaturated aliphatic bridge and/or the aryl or heteroaryl radical can be part of a polycyclic system, are particularly preferred.

Pharmaceutical formulations comprising at least one compound corresponding to formula II-VII wherein R³ represents a linear or branched, saturated or unsaturated aliphatic $C_{1-6}$ radical, a saturated or unsaturated cycloaliphatic $C_{3-7}$ radical, a phenyl radical or a five- or six-membered heteroaryl radical, wherein the particular ring system optionally can be mono- or polysubstituted and/or can be bonded via a linear or branched, saturated or unsaturated aliphatic $C_{1-5}$ bridge and the other symbols have the abovementioned meaning, are furthermore preferred.

Pharmaceutical formulations comprising at least one compound corresponding to formula II-VII wherein R³ represents a linear or branched, saturated or unsaturated aliphatic $C_{1-3}$ radical, a saturated or unsaturated cycloaliphatic $C_{5-6}$ radical, a phenyl radical or a five- or six-membered heteroaryl radical, wherein the particular ring system optionally can be mono- or polysubstituted by halogen, an alkyl group, an alkoxy group and/or a trihalogenated alkyl group and/or can be bonded via a linear or branched, saturated or unsaturated aliphatic $C_{1-3}$ bridge, and the other symbols have the abovementioned meaning are furthermore preferred.

Pharmaceutical formulations comprising at least one compound corresponding to formula II-VII wherein R³ represents a vinyl radical, a cyclopentyl radical, a cyclohexyl radical, a thiophenyl radical or a phenyl radical, wherein the cyclohexyl radical optionally can be bonded via a methylene bridge or the phenyl radical optionally can be mono- or polysubstituted by fluorine, chlorine, a methyl group, an isopropyl group, a methoxy group and/or a trifluoromethyl group and/or optionally can be bonded via a linear, saturated aliphatic $C_{1-3}$ bridge or an ethynyl bridge, and the other symbols have the abovementioned meaning, are furthermore preferred.

A heteroaryl radical is understood as meaning an optionally mono- or polysubstituted, five- or six-membered aromatic radical, which can be part of a polycyclic system, having at least one, optionally 2, 3, 4 or 5 heteroatoms, which can be identical or different. Preferred heteroatoms are nitrogen, oxygen and sulfur. Heteroaryl radicals chosen from the group comprising the pyrrolyl, indolyl, furyl, (furanyl), benzofuranyl, thienyl (thiophenyl), benzothienyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl and phenothiazinyl radical are particularly preferred. Bonding can be via any desired ring atom which is capable of bonding. The substituents optionally present can be identical or different and bonded to any desired ring atom which is capable of bonding.

An aryl radical is understood as meaning an optionally mono- or polysubstituted, aromatic radical, which can be part of a polycyclic system. A phenyl radical is particularly preferred. Bonding can be via any desired ring atom which is capable of bonding. The substituents optionally present can be identical or different and bonded to any desired ring atom which is capable of bonding.

Pharmaceutical formulations which are very particularly preferred are those comprising at least one compound chosen from the group comprising 2-methyl-1-(4-methyl-piperazin-1-yl)-3-phenyl-pentan-3-ol;
3-(4-chloro-phenyl)-2-methyl-1-(4-methyl-piperazin-1-yl)-pentan-3-ol;
3-benzyl-2-methyl-1-(4-methyl-piperazin-1-yl)-pentan-3-ol;
3-(4-fluoro-3-methyl-phenyl)-2-methyl-1-(4-methyl-piperazin-1-yl)-pentan-3-ol;
2-methyl-1-(4-methyl-piperazin-1-yl)-3-o-tolyl-pentan-3-ol;
3-ethyl-4-methyl-5-(4-methyl-piperazin-1-yl)-pent-1-en-3-ol;
3-(4-tert-butyl-phenyl)-2-methyl-1-(4-methyl-piperazin-1-yl)-pentan-3-ol;
3-cyclopentyl-2-methyl-1-(4-methyl-piperazin-1-yl)-pentan-3-ol;
2-methyl-1-(4-methyl-piperazin-1-yl)-3-m-tolyl-pentan-3-ol;
3-cyclohexyl-2-methyl-1-(4-methyl-piperazin-1-yl)-pentan-3-ol;
3-(4-fluoro-phenyl)-2-methyl-1-(4-methyl-piperazin-1-yl)-pentan-3-ol;
3-ethyl-2-methyl-1-(4-methyl-piperazin-1-yl)-5-phenyl-pentan-3-ol;
3-ethyl-4-methyl-5-(4-methyl-piperazin-1-yl)-1-phenyl-pent-1-yn-3-ol;
2-methyl-1-(4-methyl-piperazin-1-yl)-3-thiophen-2-yl-pentan-3-ol;
3-(3-methoxy-phenyl)-2-methyl-1-(4-methyl-piperazin-1-yl)-pentan-3-ol;
3-ethyl-2-methyl-1-(4-methyl-piperazin-1-yl)-6-phenyl-hexan-3-ol;
2-methyl-1-(4-methyl-piperazin-1-yl)-3-p-tolyl-pentan-3-ol;
3-(4-methoxy-phenyl)-2-methyl-1-(4-methyl-piperazin-1-yl)-pentan-3-ol;
2-(4-methyl-piperazin-1-ylmethyl)-1-phenyl-cyclohexanol;
1-benzyl-2-(4-methyl-piperazin-1-ylmethyl)-cyclohexanol;
1-(4-fluoro-3-methyl-phenyl)-2-(4-methyl-piperazin-1-ylmethyl)-cyclohexanol;
2-(4-methyl-piperazin-1-ylmethyl)-1-o-tolyl-cyclohexanol;
2-(4-methyl-piperazin-1-ylmethyl)-1-vinyl-cyclohexanol;
1-cyclopentyl-2-(4-methyl-piperazin-1-ylmethyl)-cyclohexanol;
2-(4-methyl-piperazin-1-ylmethyl)-1-m-tolyl-cyclohexanol;
2-(4-methyl-piperazin-1-ylmethyl)-bicyclohexyl-1-ol;
1-(4-fluoro-phenyl)-2-(4-methyl-piperazin-1-ylmethyl)-cyclohexanol;
2-(4-methyl-piperazin-1-ylmethyl)-1-phenethyl-cyclohexanol;
2-(4-methyl-piperazin-1-ylmethyl)-1-thiophen-2-yl-cyclohexanol;
1-(2,4-dichloro-phenyl)-2-(4-methyl-piperazin-1-ylmethyl)-cyclohexanol;
1-(3-methoxy-phenyl)-2-(4-methyl-piperazin-1-ylmethyl)-cyclohexanol;
2-(4-methyl-piperazin-1-ylmethyl)-1-(3-phenyl-propyl)-cyclohexanol;
2-(4-methyl-piperazin-1-ylmethyl)-1-p-tolyl-cyclohexanol;
1-(4-methoxy-phenyl)-2-(4-methyl-piperazin-1-ylmethyl)-cyclohexanol;
1-benzyl-2-(4-methyl-piperazin-1-ylmethyl)-cyclooctanol;
2-(4-methyl-piperazin-1-ylmethyl)-1-vinyl-cyclooctanol;
1-(4-tert-butyl-phenyl)-2-(4-methyl-piperazin-1-ylmethyl)-cyclooctanol;
1-cyclopentyl-2-(4-methyl-piperazin-1-ylmethyl)-cyclooctanol;
2-(4-methyl-piperazin-1-ylmethyl)-1-phenethyl-cyclooctanol;
2-(4-methyl-piperazin-1-ylmethyl)-1-phenylethynyl-cyclooctanol;
2-(4-methyl-piperazin-1-ylmethyl)-1-thiophen-2-yl-cyclooctanol;
1-(3-methoxy-phenyl)-2-(4-methyl-piperazin-1-ylmethyl)-cyclooctanol;
2-(4-methyl-piperazin-1-ylmethyl)-1-(3-phenyl-propyl)-cyclooctanol;
2-(4-methyl-piperazin-1-ylmethyl)-1-p-tolyl-cyclooctanol;
1-(4-methoxy-phenyl)-2-(4-methyl-piperazin-1-ylmethyl)-cyclooctanol;
2-(4-methyl-piperazin-1-ylmethyl)-1-phenyl-cycloheptanol;
1-(4-chloro-phenyl)-2-(4-methyl-piperazin-1-ylmethyl)-cycloheptanol;
1-benzyl-2-(4-methyl-piperazin-1-ylmethyl)-cycloheptanol;
1-(4-fluoro-3-methyl-phenyl)-2-(4-methyl-piperazin-1-ylmethyl)-cycloheptanol;
2-(4-methyl-piperazin-1-ylmethyl)-1-o-tolyl-cycloheptanol;
2-(4-methyl-piperazin-1-ylmethyl)-1-vinyl-cycloheptanol;
1-(4-tert-butyl-phenyl)-2-(4-methyl-piperazin-1-ylmethyl)-cycloheptanol;
1-cyclopentyl-2-(4-methyl-piperazin-1-ylmethyl)-cycloheptanol;
2-(4-methyl-piperazin-1-ylmethyl)-1-m-tolyl-cycloheptanol;
1-[4-(3-chloro-phenyl)-piperazin-1-yl]-2-methyl-3-phenyl-pentan-3-ol;
3-(4-chloro-phenyl)-1-[4-(3-chloro-phenyl)-piperazin-1-yl]-2-methyl-pentan-3-ol;
3-benzyl-1-[4-(3-chloro-phenyl)-piperazin-1-yl]-2-methyl-pentan-3-ol;
1-[4-(3-chloro-phenyl)-piperazin-1-yl]-3-(4-fluoro-3-methyl-phenyl)-2-methyl-pentan-3-ol;
5-[4-(3-chloro-phenyl)-piperazin-1-yl]-3-ethyl-4-methyl-pent-1-en-3-ol;
3-(4-tert-butyl-phenyl)-1-[4-(3-chloro-phenyl)-piperazin-1-yl]-2-methyl-pentan-3-ol;
1-[4-(3-chloro-phenyl)-piperazin-1-yl]-2-methyl-3-m-tolyl-pentan-3-ol;

1-[4-(3-chloro-phenyl)-piperazin-1-yl]-3-cyclohexyl-2-methyl-pentan-3-ol;
1-[4-(3-chloro-phenyl)-piperazin-1-yl]-3-(4-fluoro-phenyl)-2-methyl-pentan-3-ol;
1-[4-(3-chloro-phenyl)-piperazin-1-yl]-3-ethyl-2-methyl-5-phenyl-pentan-3-ol;
5-[4-(3-chloro-phenyl)-piperazin-1-yl]-3-ethyl-4-methyl-1-phenyl-pent-1-yn-3-ol;
1-[4-(3-chloro-phenyl)-piperazin-1-yl]-2-methyl-3-thiophen-2-yl-pentan-3-ol;
1-[4-(3-chloro-phenyl)-piperazin-1-yl]-3-(3-methoxy-phenyl)-2-methyl-pentan-3-ol;
1-[4-(3-chloro-phenyl)-piperazin-1-yl]-3-ethyl-2-methyl-6-phenyl-hexan-3-ol;
1-[4-(3-chloro-phenyl)-piperazin-1-yl]-2-methyl-3-p-tolyl-pentan-3-ol;
1-[4-(3-chloro-phenyl)-piperazin-1-yl]-3-(4-methoxy-phenyl)-2-methyl-pentan-3-ol;
1-[4-(3-chloro-phenyl)-piperazin-1-yl]-3-(5-fluoro-2-methoxy-phenyl)-2-methyl-pentan-3-ol;
1-[4-(3-chloro-phenyl)-piperazin-1-yl]-3-(3-fluoro-phenyl)-2-methyl-pentan-3-ol;
3-(3-chloro-phenyl)-1-[4-(3-chloro-phenyl)-piperazin-1-yl]-2-methyl-pentan-3-ol;
3-(2-chloro-benzyl)-1-[4-(3-chloro-phenyl)-piperazin-1-yl]-2-methyl-pentan-3-ol;
1-[4-(3-chloro-phenyl)-piperazin-1-yl]-3-(4-fluoro-benzyl)-2-methyl-pentan-3-ol;
1-[4-(3-chloro-phenyl)-piperazin-1-yl]-3-(3-methoxy-benzyl)-2-methyl-pentan-3-ol;
1-[4-(3-chloro-phenyl)-piperazin-1-yl]-3-(3-fluoro-benzyl)-2-methyl-pentan-3-ol;
1-[4-(3-chloro-phenyl)-piperazin-1-yl]-3-(2-methoxy-phenyl)-2-methyl-pentan-3-ol;
1-[4-(3-chloro-phenyl)-piperazin-1-yl]-2-methyl-3-(2-methyl-benzyl)-pentan-3-ol;
1-[4-(3-chloro-phenyl)-piperazin-1-yl]-2-methyl-3-(3-trifluoromethyl-phenyl)-pentan-3-ol;
1-[4-(3-chloro-phenyl)-piperazin-1-yl]-2-methyl-3-(3-methyl-benzyl)-pentan-3-ol;
3-(4-chloro-benzyl)-1-[4-(3-chloro-phenyl)-piperazin-1-yl]-2-methyl-pentan-3-ol;
3-(2-chloro-6-fluoro-benzyl)-1-[4-(3-chloro-phenyl)-piperazin-1-yl]-2-methyl-pentan-3-ol;
1-[4-(3-chloro-phenyl)-piperazin-1-yl]-3-(2,5-dimethyl-benzyl)-2-methyl-pentan-3-ol;
3-(3-chloro-benzyl)-1-[4-(3-chloro-phenyl)-piperazin-1-yl]-2-methyl-pentan-3-ol;
1-[4-(3-chloro-phenyl)-piperazin-1-yl]-3-(2,4-dichloro-benzyl)-2-methyl-pentan-3-ol;
3-cyclohexylmethyl-2-methyl-1-(4-methyl-piperazin-1-yl)-pentan-3-ol;
3-(5-fluoro-2-methoxy-phenyl)-2-methyl-1-(4-methyl-piperazin-1-yl)-pentan-3-ol;
3-(3-fluoro-phenyl)-2-methyl-1-(4-methyl-piperazin-1-yl)-pentan-3-ol;
3-(3-chloro-phenyl)-2-methyl-1-(4-methyl-piperazin-1-yl)-pentan-3-ol;
3-(3,5-dichloro-phenyl)-2-methyl-1-(4-methyl-piperazin-1-yl)-pentan-3-ol;
3-(2-chloro-benzyl)-2-methyl-1-(4-methyl-piperazin-1-yl)-pentan-3-ol;
3-(4-fluoro-benzyl)-2-methyl-1-(4-methyl-piperazin-1-yl)-pentan-3-ol;
3-(3-methoxy-benzyl)-2-methyl-1-(4-methyl-piperazin-1-yl)-pentan-3-ol;
3-(4-chloro-3-trifluoromethyl-phenyl)-2-methyl-1-(4-methyl-piperazin-1-yl)-pentan-3-ol;
3-(3-fluoro-benzyl)-2-methyl-1-(4-methyl-piperazin-1-yl)-pentan-3-ol;
3-(2-methoxy-phenyl)-2-methyl-1-(4-methyl-piperazin-1-yl)-pentan-3-ol;
2-methyl-3-(2-methyl-benzyl)-1-(4-methyl-piperazin-1-yl)-pentan-3-ol;
3-(3-chloro-4-fluoro-phenyl)-2-methyl-1-(4-methyl-piperazin-1-yl)-pentan-3-ol;
2-methyl-1-(4-methyl-piperazin-1-yl)-3-(3-trifluoromethyl-phenyl)-pentan-3-ol;
2-methyl-3-(3-methyl-benzyl)-1-(4-methyl-piperazin-1-yl)-pentan-3-ol;
3-(4-chloro-benzyl)-2-methyl-1-(4-methyl-piperazin-1-yl)-pentan-3-ol;
3-(2-chloro-6-fluoro-benzyl)-2-methyl-1-(4-methyl-piperazin-1-yl)-pentan-3-ol;
3-(2,5-dimethyl-benzyl)-2-methyl-1-(4-methyl-piperazin-1-yl)-pentan-3-ol;
3-(3-chloro-benzyl)-2-methyl-1-(4-methyl-piperazin-1-yl)-pentan-3-ol;
3-(2,4-dichloro-benzyl)-2-methyl-1-(4-methyl-piperazin-1-yl)-pentan-3-ol;
1-cyclohexylmethyl-2-(4-methyl-piperazin-1-ylmethyl)-cyclohexanol;
1-(5-fluoro-2-methoxy-phenyl)-2-(4-methyl-piperazin-1-ylmethyl)-cyclohexanol;
1-(3-fluoro-phenyl)-2-(4-methyl-piperazin-1-ylmethyl)-cyclohexanol;
1-(3-chloro-phenyl)-2-(4-methyl-piperazin-1-ylmethyl)-cyclohexanol;
1-(3,5-dichloro-phenyl)-2-(4-methyl-piperazin-1-ylmethyl)-cyclohexanol;
1-(2-chloro-benzyl)-2-(4-methyl-piperazin-1-ylmethyl)-cyclohexanol;
1-(4-fluoro-benzyl)-2-(4-methyl-piperazin-1-ylmethyl)-cyclohexanol;
1-(3-methoxy-benzyl)-2-(4-methyl-piperazin-1-ylmethyl)-cyclohexanol;
1-(4-chloro-3-trifluoromethyl-phenyl)-2-(4-methyl-piperazin-1-ylmethyl)-cyclohexanol;
1-(3-fluoro-benzyl)-2-(4-methyl-piperazin-1-ylmethyl)-cyclohexanol;
1-(2-methoxy-phenyl)-2-(4-methyl-piperazin-1-ylmethyl)-cyclohexanol;
1-(2-methyl-benzyl)-2-(4-methyl-piperazin-1-ylmethyl)-cyclohexanol;
1-(3-chloro-4-fluoro-phenyl)-2-(4-methyl-piperazin-1-ylmethyl)-cyclohexanol;
2-(4-methyl-piperazin-1-ylmethyl)-1-(3-trifluoromethyl-phenyl)-cyclohexanol;
1-(3-methyl-benzyl)-2-(4-methyl-piperazin-1-ylmethyl)-cyclohexanol;
1-(4-chloro-benzyl)-2-(4-methyl-piperazin-1-ylmethyl)-cyclohexanol;
1-(2,5-dimethyl-benzyl)-2-(4-methyl-piperazin-1-ylmethyl)-cyclohexanol;
1-(3-chloro-benzyl)-2-(4-methyl-piperazin-1-ylmethyl)-cyclohexanol;
1-(2,4-dichloro-benzyl)-2-(4-methyl-piperazin-1-ylmethyl)-cyclohexanol;
1-cyclohexylmethyl-2-(4-methyl-piperazin-1-ylmethyl)-cyclooctanol;
1-(5-fluoro-2-methoxy-phenyl)-2-(4-methyl-piperazin-1-ylmethyl)-cyclooctanol;

1-(2-chloro-benzyl)-2-(4-methyl-piperazin-1-ylmethyl)-cyclooctanol;
1-(4-fluoro-benzyl)-2-(4-methyl-piperazin-1-ylmethyl)-cyclooctanol;
1-(3-fluoro-benzyl)-2-(4-methyl-piperazin-1-ylmethyl)-cyclooctanol;
1-(2-methoxy-phenyl)-2-(4-methyl-piperazin-1-ylmethyl)-cyclooctanol;
1-(3-methyl-benzyl)-2-(4-methyl-piperazin-1-ylmethyl)-cyclooctanol;
1-(4-chloro-benzyl)-2-(4-methyl-piperazin-1-ylmethyl)-cyclooctanol;
1-(2-chloro-6-fluoro-benzyl)-2-(4-methyl-piperazin-1-ylmethyl)-cyclooctanol;
1-(2,5-dimethyl-benzyl)-2-(4-methyl-piperazin-1-ylmethyl)-cyclooctanol;
1-(3-chloro-benzyl)-2-(4-methyl-piperazin-1-ylmethyl)-cyclooctanol;
1-(2,4-dichloro-benzyl)-2-(4-methyl-piperazin-1-ylmethyl)-cyclooctanol;
1-cyclohexylmethyl-2-(4-methyl-piperazin-1-ylmethyl)-cycloheptanol;
1-(5-fluoro-2-methoxy-phenyl)-2-(4-methyl-piperazin-1-ylmethyl)-cycloheptanol;
1-(3-fluoro-phenyl)-2-(4-methyl-piperazin-1-ylmethyl)-cycloheptanol;
1-(3-chloro-phenyl)-2-(4-methyl-piperazin-1-ylmethyl)-cycloheptanol;
1-(3,5-dichloro-phenyl)-2-(4-methyl-piperazin-1-ylmethyl)-cycloheptanol;
1-(2-chloro-benzyl)-2-(4-methyl-piperazin-1-ylmethyl)-cycloheptanol;
1-(4-fluoro-benzyl)-2-(4-methyl-piperazin-1-ylmethyl)-cycloheptanol;
1-(3-methoxy-benzyl)-2-(4-methyl-piperazin-1-ylmethyl)-cycloheptanol;
1-(4-chloro-3-trifluoromethyl-phenyl)-2-(4-methyl-piperazin-1-ylmethyl)-cycloheptanol;
1-(3-fluoro-benzyl)-2-(4-methyl-piperazin-1-ylmethyl)-cycloheptanol;
1-(2-methoxy-phenyl)-2-(4-methyl-piperazin-1-ylmethyl)-cycloheptanol;
1-(2-methyl-benzyl)-2-(4-methyl-piperazin-1-ylmethyl)-cycloheptanol;
1-(3-chloro-4-fluoro-phenyl)-2-(4-methyl-piperazin-1-ylmethyl)-cycloheptanol;
2-(4-methyl-piperazin-1-ylmethyl)-1-(3-trifluoromethyl-phenyl)-cycloheptanol;
1-(3-methyl-benzyl)-2-(4-methyl-piperazin-1-ylmethyl)-cycloheptanol;
1-(4-chloro-benzyl)-2-(4-methyl-piperazin-1-ylmethyl)-cycloheptanol;
1-(2-chloro-6-fluoro-benzyl)-2-(4-methyl-piperazin-1-ylmethyl)-cycloheptanol;
1-(2,5-dimethyl-benzyl)-2-(4-methyl-piperazin-1-ylmethyl)-cycloheptanol;
1-(3-chloro-benzyl)-2-(4-methyl-piperazin-1-ylmethyl)-cycloheptanol;
1-(2,4-dichloro-benzyl)-2-(4-methyl-piperazin-1-ylmethyl)-cycloheptanol;
1-benzyl-2-(4-methyl-piperazin-1-ylmethyl)-cyclododecanol;
2-(4-methyl-piperazin-1-ylmethyl)-1-vinyl-cyclododecanol;
1-cyclopentyl-2-(4-methyl-piperazin-1-ylmethyl)-cyclododecanol;
2-(4-methyl-piperazin-1-ylmethyl)-1-phenethyl-cyclododecanol;
2-(4-methyl-piperazin-1-ylmethyl)-1-phenylethynyl-cyclododecanol;
2-(4-methyl-piperazin-1-ylmethyl)-1-thiophen-2-yl-cyclododecanol;
2-(4-methyl-piperazin-1-ylmethyl)-1-(3-phenyl-propyl)-cyclododecanol;
1-(5-fluoro-2-methoxy-phenyl)-2-(4-methyl-piperazin-1-ylmethyl)-cyclododecanol;
1-(2-chloro-benzyl)-2-(4-methyl-piperazin-1-ylmethyl)-cyclododecanol;
1-(4-fluoro-benzyl)-2-(4-methyl-piperazin-1-ylmethyl)-cyclododecanol;
1-(3-methoxy-benzyl)-2-(4-methyl-piperazin-1-ylmethyl)-cyclododecanol;
1-(3-fluoro-benzyl)-2-(4-methyl-piperazin-1-ylmethyl)-cyclododecanol;
1-(2-methoxy-phenyl)-2-(4-methyl-piperazin-1-ylmethyl)-cyclododecanol;
1-(2-methyl-benzyl)-2-(4-methyl-piperazin-1-ylmethyl)-cyclododecanol;
1-(3-methyl-benzyl)-2-(4-methyl-piperazin-1-ylmethyl)-cyclododecanol;
1-(4-chloro-benzyl)-2-(4-methyl-piperazin-1-ylmethyl)-cyclododecanol;
1-(2,5-dimethyl-benzyl)-2-(4-methyl-piperazin-1-ylmethyl)-cyclododecanol;
1-(3-chloro-benzyl)-2-(4-methyl-piperazin-1-ylmethyl)-cyclododecanol;
1-(2,4-dichloro-benzyl)-2-(4-methyl-piperazin-1-ylmethyl)-cyclododecanol;
2-[4-(3-chloro-phenyl)-piperazin-1-ylmethyl]-1-cyclohexylmethyl-cyclohexanol;
2-[4-(3-chloro-phenyl)-piperazin-1-ylmethyl]-1-(5-fluoro-2-methoxy-phenyl)-cyclohexanol;
2-[4-(3-chloro-phenyl)-piperazin-1-ylmethyl]-1-(3-fluoro-phenyl)-cyclohexanol;
1-(3-chloro-phenyl)-2-[4-(3-chloro-phenyl)-piperazin-1-ylmethyl]-cyclohexanol;
2-[4-(3-chloro-phenyl)-piperazin-1-ylmethyl]-1-(3,5-dichloro-phenyl)-cyclohexanol;
1-(2-chloro-benzyl)-2-[4-(3-chloro-phenyl)-piperazin-1-ylmethyl]-cyclohexanol;
2-[4-(3-chloro-phenyl)-piperazin-1-ylmethyl]-1-(4-fluoro-benzyl)-cyclohexanol;
2-[4-(3-chloro-phenyl)-piperazin-1-ylmethyl]-1-(4-chloro-3-trifluoromethylphenyl)-cyclohexanol;
2-[4-(3-chloro-phenyl)-piperazin-1-ylmethyl]-1-(3-fluoro-benzyl)-cyclohexanol;
2-[4-(3-chloro-phenyl)-piperazin-1-ylmethyl]-1-(2-methoxy-phenyl)-cyclohexanol;
1-(3-chloro-4-fluoro-phenyl)-2-[4-(3-chloro-phenyl)-piperazin-1-ylmethyl]-cyclohexanol;
2-[4-(3-chloro-phenyl)-piperazin-1-ylmethyl]-1-(3-trifluoromethyl-phenyl)-cyclohexanol;
2-[4-(3-chloro-phenyl)-piperazin-1-ylmethyl]-1-(3-methyl-benzyl)-cyclohexanol;
1-(4-chloro-benzyl)-2-[4-(3-chloro-phenyl)-piperazin-1-ylmethyl]-cyclohexanol;
1-(2-chloro-6-fluoro-benzyl)-2-[4-(3-chloro-phenyl)-piperazin-1-ylmethyl]-cyclohexanol;
2-[4-(3-chloro-phenyl)-piperazin-1-ylmethyl]-1-(2,5-dimethyl-benzyl)-cyclohexanol;
1-(3-chloro-benzyl)-2-[4-(3-chloro-phenyl)-piperazin-1-ylmethyl]-cyclohexanol;
2-[4-(2-chloro-phenyl)-piperazin-1-ylmethyl]-1-phenyl-cyclohexanol;

1-(4-chloro-phenyl)-2-[4-(2-chloro-phenyl)-piperazin-1-ylmethyl]-cyclohexanol;
1-benzyl-2-[4-(2-chloro-phenyl)-piperazin-1-ylmethyl]-cyclohexanol;
2-[4-(2-chloro-phenyl)-piperazin-1-ylmethyl]-1-(4-fluoro-3-methyl-phenyl)-cyclohexanol;
2-[4-(2-chloro-phenyl)-piperazin-1-ylmethyl]-1-o-tolyl-cyclohexanol;
2-[4-(2-chloro-phenyl)-piperazin-1-ylmethyl]-1-vinyl-cyclohexanol;
1-(4-tert-butyl-phenyl)-2-[4-(2-chloro-phenyl)-piperazin-1-ylmethyl]-cyclohexanol;
2-[4-(2-chloro-phenyl)-piperazin-1-ylmethyl]-1-cyclopentyl-cyclohexanol;
2-[4-(2-chloro-phenyl)-piperazin-1-ylmethyl]-1-m-tolyl-cyclohexanol;
2-[4-(2-chloro-phenyl)-piperazin-1-ylmethyl]-bicyclohexyl-1-ol;
2-[4-(2-chloro-phenyl)-piperazin-1-ylmethyl]-1-(4-fluoro-phenyl)-cyclohexanol;
2-[4-(2-chloro-phenyl)-piperazin-1-ylmethyl]-1-phenethyl-cyclohexanol;
2-[4-(2-chloro-phenyl)-piperazin-1-ylmethyl]-1-phenylethynyl-cyclohexanol;
2-[4-(2-chloro-phenyl)-piperazin-1-ylmethyl]-1-thiophen-2-yl-cyclohexanol;
2-[4-(2-chloro-phenyl)-piperazin-1-ylmethyl]-1-(3-methoxy-phenyl)-cyclohexanol;
2-[4-(2-chloro-phenyl)-piperazin-1-ylmethyl]-1-(3-phenyl-propyl)-cyclohexanol;
2-[4-(2-chloro-phenyl)-piperazin-1-ylmethyl]-1-p-tolyl-cyclohexanol;
2-[4-(2-chloro-phenyl)-piperazin-1-ylmethyl]-1-(4-methoxy-phenyl)-cyclohexanol;
2-[4-(2-chloro-phenyl)-piperazin-1-ylmethyl]-1-cyclohexylmethyl-cyclohexanol;
2-[4-(2-chloro-phenyl)-piperazin-1-ylmethyl]-1-(5-fluoro-2-methoxy-phenyl)-cyclohexanol;
1-(3-chloro-phenyl)-2-[4-(2-chloro-phenyl)-piperazin-1-ylmethyl]-cyclohexanol;
2-[4-(2-chloro-phenyl)-piperazin-1-ylmethyl]-1-(3,5-dichloro-phenyl)-cyclohexanol;
1-(2-chloro-benzyl)-2-[4-(2-chloro-phenyl)-piperazin-1-ylmethyl]-cyclohexanol;
2-[4-(2-chloro-phenyl)-piperazin-1-ylmethyl]-1-(4-fluoro-benzyl)-cyclohexanol;
2-[4-(2-chloro-phenyl)-piperazin-1-ylmethyl]-1-(3-methoxy-benzyl)-cyclohexanol;
2-[4-(2-chloro-phenyl)-piperazin-1-ylmethyl]-1-(4-chloro-3-trifluoromethyl-phenyl)-cyclohexanol;
2-[4-(2-chloro-phenyl)-piperazin-1-ylmethyl]-1-(3-fluoro-benzyl)-cyclohexanol;
2-[4-(2-chloro-phenyl)-piperazin-1-ylmethyl]-1-(2-methoxy-phenyl)-cyclohexanol;
2-[4-(2-chloro-phenyl)-piperazin-1-ylmethyl]-1-(2-methyl-benzyl)-cyclohexanol;
1-(3-chloro-4-fluoro-phenyl)-2-[4-(2-chloro-phenyl)-piperazin-1-ylmethyl]-cyclohexanol;
2-[4-(2-chloro-phenyl)-piperazin-1-ylmethyl]-1-(3-trifluoromethyl-phenyl)-cyclohexanol;
2-[4-(2-chloro-phenyl)-piperazin-1-ylmethyl]-1-(3-methyl-benzyl)-cyclohexanol;
1-(4-chloro-benzyl)-2-[4-(2-chloro-phenyl)-piperazin-1-ylmethyl]-cyclohexanol;
1-(2-chloro-6-fluoro-benzyl)-2-[4-(2-chloro-phenyl)-piperazin-1-ylmethyl]-cyclohexanol;
2-[4-(2-chloro-phenyl)-piperazin-1-ylmethyl]-1-(2,5-dimethyl-benzyl)-cyclohexanol;
1-(3-chloro-benzyl)-2-[4-(2-chloro-phenyl)-piperazin-1-ylmethyl]-cyclohexanol;
2-[4-(2-chloro-phenyl)-piperazin-1-ylmethyl]-1-(2,4-dichloro-benzyl)-cyclohexanol;
2-[4-(2-methoxy-phenyl)-piperazin-1-ylmethyl]-1-phenyl-cyclohexanol;
1-(4-chloro-phenyl)-2-[4-(2-methoxy-phenyl)-piperazin-1-ylmethyl]-cyclohexanol;
1-benzyl-2-[4-(2-methoxy-phenyl)-piperazin-1-ylmethyl]-cyclohexanol;
1-(4-fluoro-3-methyl-phenyl)-2-[4-(2-methoxy-phenyl)-piperazin-1-ylmethyl]-cyclohexanol;
2-[4-(2-methoxy-phenyl)-piperazin-1-ylmethyl]-1-o-tolyl-cyclohexanol;
2-[4-(2-methoxy-phenyl)-piperazin-1-ylmethyl]-1-vinyl-cyclohexanol;
1-(4-tert-butyl-phenyl)-2-[4-(2-methoxy-phenyl)-piperazin-1-ylmethyl]-cyclohexanol;
1-cyclopentyl-2-[4-(2-methoxy-phenyl)-piperazin-1-ylmethyl]-cyclohexanol;
2-[4-(2-methoxy-phenyl)-piperazin-1-ylmethyl]-1-m-tolyl-cyclohexanol;
2-[4-(2-methoxy-phenyl)-piperazin-1-ylmethyl]-bicyclohexyl-1-ol;
1-(4-fluoro-phenyl)-2-[4-(2-methoxy-phenyl)-piperazin-1-ylmethyl]-cyclohexanol;
2-[4-(2-methoxy-phenyl)-piperazin-1-ylmethyl]-1-phenethyl-cyclohexanol;
2-[4-(2-methoxy-phenyl)-piperazin-1-ylmethyl]-1-phenylethynyl-cyclohexanol;
2-[4-(2-methoxy-phenyl)-piperazin-1-ylmethyl]-1-thiophen-2-yl-cyclohexanol;
1-(3-methoxy-phenyl)-2-[4-(2-methoxy-phenyl)-piperazin-1-ylmethyl]-cyclohexanol;
2-[4-(2-methoxy-phenyl)-piperazin-1-ylmethyl]-1-(3-phenyl-propyl)-cyclohexanol;
1-(2,3-dichloro-phenyl)-2-[4-(2-methoxy-phenyl)-piperazin-1-ylmethyl]-cyclohexanol;
2-[4-(2-methoxy-phenyl)-piperazin-1-ylmethyl]-1-p-tolyl-cyclohexanol;
1-(4-methoxy-phenyl)-2-[4-(2-methoxy-phenyl)-piperazin-1-ylmethyl]-cyclohexanol;
1-cyclohexylmethyl-2-[4-(2-methoxy-phenyl)-piperazin-1-ylmethyl]-cyclohexanol;
1-(5-fluoro-2-methoxy-phenyl)-2-[4-(2-methoxy-phenyl)-piperazin-1-ylmethyl]-cyclohexanol;
1-(3-fluoro-phenyl)-2-[4-(2-methoxy-phenyl)-piperazin-1-ylmethyl]-cyclohexanol;
1-(3-chloro-phenyl)-2-[4-(2-methoxy-phenyl)-piperazin-1-ylmethyl]-cyclohexanol;
1-(3,5-dichloro-phenyl)-2-[4-(2-methoxy-phenyl)-piperazin-1-ylmethyl]-cyclohexanol;
1-(2-chloro-benzyl)-2-[4-(2-methoxy-phenyl)-piperazin-1-ylmethyl]-cyclohexanol;
1-(4-fluoro-benzyl)-2-[4-(2-methoxy-phenyl)-piperazin-1-ylmethyl]-cyclohexanol;
1-(3-methoxy-benzyl)-2-[4-(2-methoxy-phenyl)-piperazin-1-ylmethyl]-cyclohexanol;
1-(4-chloro-3-trifluoromethyl-phenyl)-2-[4-(2-methoxy-phenyl)-piperazin-1-ylmethyl]-cyclohexanol;
1-(3-fluoro-benzyl)-2-[4-(2-methoxy-phenyl)-piperazin-1-ylmethyl]-cyclohexanol;
1-(2-methoxy-phenyl)-2-[4-(2-methoxy-phenyl)-piperazin-1-ylmethyl]-cyclohexanol;

2-[4-(2-methoxy-phenyl)-piperazin-1-ylmethyl]-1-(2-methyl-benzyl)-cyclohexanol;
1-(3-chloro-4-fluoro-phenyl)-2-[4-(2-methoxy-phenyl)-piperazin-1-ylmethyl]-cyclohexanol;
2-[4-(2-methoxy-phenyl)-piperazin-1-ylmethyl]-1-(3-trifluoromethyl-phenyl)-cyclohexanol;
2-[4-(2-methoxy-phenyl)-piperazin-1-ylmethyl]-1-(3-methyl-benzyl)-cyclohexanol;
1-(4-chloro-benzyl)-2-[4-(2-methoxy-phenyl)-piperazin-1-ylmethyl]-cyclohexanol;
1-(2-chloro-6-fluoro-benzyl)-2-[4-(2-methoxy-phenyl)-piperazin-1-ylmethyl]-cyclohexanol;
1-(2,5-dimethyl-benzyl)-2-[4-(2-methoxy-phenyl)-piperazin-1-ylmethyl]-cyclohexanol;
1-(3-chloro-benzyl)-2-[4-(2-methoxy-phenyl)-piperazin-1-ylmethyl]-cyclohexanol;
1-(2,4-dichloro-benzyl)-2-[4-(2-methoxy-phenyl)-piperazin-1-ylmethyl]-cyclohexanol;
1-benzyl-2-[4-(2-methoxy-phenyl)-piperazin-1-ylmethyl]-cyclododecanol;
2-[4-(2-methoxy-phenyl)-piperazin-1-ylmethyl]-1-vinyl-cyclododecanol;
1-phenethyl-2-[phenyl-(4-phenyl-piperazin-1-yl)-methyl]-cyclohexanol;
1-benzyl-2-[(4-methyl-piperazin-1-yl)-phenyl-methyl]-cyclohexanol;
1-benzyl-2-[phenyl-(4-phenyl-piperazin-1-yl)-methyl]-cyclohexanol;
2-[(4-methyl-piperazin-1-yl)-phenyl-methyl]-1-phenethyl-cyclohexanol;
2-[4-(2-methoxy-phenyl)-piperazin-1-ylmethyl]-1-phenethyl-cyclododecanol;

in the form of the diastereomer, the enantiomer or a mixture thereof—including the racemate—and in the form of the corresponding base, the corresponding salt and the corresponding solvate.

The pharmaceutical formulations according to the invention are preferably suitable for treatment of pain, in particular neuropathic, chronic and/or acute pain, for treatment of symptoms associated in particular with neuropathic pain, and/or other related indications, for treatment of migraine, hyperalgesia and/or allodynia, in particular thermal hyperalgesia, mechanical hyperalgesia, mechanical allodynia and/or cold allodynia, for treatment of inflammatory and/or postoperative pain, for treatment of neurodegenerative diseases, such as Alzheimer's disease, Huntington's disease, Parkinson's disease and/or epilepsy, for treatment of psychiatric and/or neuropathological disorders, such as bipolar disorders, anxiety, panic attacks, mood swings, manic behaviour, depressions and manic-depressive behaviour, for treatment of hot flashes, symptoms in the postmenopause, amyotrophic lateral sclerosis (ALS), reflex sympathetic dystrophy (RSD), spastic paralysis, restless leg syndrome, acquired nystagmus and painful diabetic neuropathy, for treatment of symptoms and/or pain caused by multiple sclerosis and/or Parkinson's disease, and for treatment of gastrointestinal damage, erythromelalgic and/or postpoliomyelitic pain and trigeminal and/or postherpetic neuralgia.

The invention also provides the use of at least one compound corresponding to formula I, preferably of the general formula II, III, IV, V, VI or VII, for the preparation of a pharmaceutical formulation for the treatment of pain, in particular neuropathic, chronic and/or acute pain, for treatment of symptoms associated in particular with neuropathic pain, and/or other related indications, for treatment of migraine, hyperalgesia and/or allodynia, in particular thermal hyperalgesia, mechanical hyperalgesia, mechanical allodynia and/or cold allodynia, for treatment of inflammatory and/or postoperative pain, for treatment of neurodegenerative diseases, such as Alzheimer's disease, Huntington's disease, Parkinson's disease and/or epilepsy, for treatment of psychiatric and/or neuropathological disorders, such as bipolar disorders, anxiety, panic attacks, mood swings, manic behaviour, depressions and manic-depressive behaviour, for treatment of hot flashes, symptoms in the postmenopause, amyotrophic lateral sclerosis (ALS), reflex sympathetic dystrophy (RSD), spastic paralysis, restless leg syndrome, acquired nystagmus and painful diabetic neuropathy, for treatment of symptoms and/or pain caused by multiple sclerosis and/or Parkinson's disease, and for treatment of gastrointestinal damage, erythromelalgic and/or postpoliomyelitic pain and trigeminal and/or postherpetic neuralgia.

The pharmaceutical formulations according to the invention can be formulated as liquid, semi-solid or solid forms, for example in the form of injection solutions, drops, juices, syrups, sprays, suspensions, tablets, patches, capsules, plasters, suppositories, ointments, creams, lotions, gels, emulsions or aerosols or in multiparticulate form, for example in the form of pellets or granules, and also administered as such.

In addition to at least one compound of the general formula I, preferably of the general formula II, III, IV, V, VI or VII, the pharmaceutical formulations according to the invention conventionally comprise further physiologically acceptable pharmaceutical auxiliary substances, which are preferably chosen from the group consisting of carrier materials, fillers, solvents, diluents, surface-active substances, dyestuffs, preservatives, disintegrating agents, slip agents, lubricants, flavourings and binders.

The choice of the physiologically acceptable auxiliary substances and the amounts thereof to be employed depends on whether the pharmaceutical formulation is to be administered orally, subcutaneously, parenterally, intravenously, intraperitoneally, intradermally, intramuscularly, intranasally, buccally, rectally or locally, for example on infections on the skin, the mucous membranes and on the eyes. Formulations in the form of tablets, coated tablets, capsules, granules, pellets, drops, juices and syrups are preferably suitable for oral administration, and solutions, suspensions, easily reconstitutable dry formulations and sprays are suitable for parenteral, topical and inhalatory administration. Compounds of the general formula I, preferably of the general formula II, III, IV, V, VI or VII, in a depot in dissolved form or in a patch, optionally with the addition of agents which promote penetration through the skin, are suitable formulations for percutaneous administration.

The pharmaceutical formulations according to the invention are prepared with the aid of conventional means, devices, methods and processes known to the expert, such as are described, for example, in A. R. Gennaro (ed.), Remington's Pharmaceutical Sciences, 17th edition, Mack Publishing Company, Easton, Pa. (1985), in particular in part 8, chapter 76 to 93. The corresponding description in the literature is incorporated herein by reference and forms part of the disclosure.

The amount of the particular compound of the general formula I, preferably of the general formula II, III, IV, V, VI or VII, to be administered to the patient can vary and depends, for example, on the weight or age of the patient and on the mode of administration, the indication and the severity of the disease. 0.005 to 500 mg/kg, preferably 0.05 to 5 mg/kg of body weight of the patient of at least one compound of the general formula I, preferably of the general formula II, III, IV, V, VI or VII, are conventionally administered.

EXAMPLES

Pharmacological Studies

In the binding assay, the binding and affinities of the compounds according to the invention to the binding site—which is also hitherto still unknown in science—of gabapentin is investigated. The affinity of the compounds was measured via the displacement of gabapentin from its binding site.

The procedure for the measurement was as follows: Homogenate aliquots were thawed and diluted 20-fold with buffer 1, resuspended and then centrifuged at 110,000×g for 20 minutes. The pellet was resuspended with buffer 2 (10 mM HEPES, 0.05% $NaN_3$, 1 tablet of Complete (Roche Diagnostics) per 100 ml, 0.004% Structol, pH 7.4) and adjusted to a protein concentration of 0.6 mg/ml. 225 μl of homogenate, 20 μl of [$^3$H]-gabapentin (76 Ci/mmol) in buffer 2, corresponding to a concentration of 10 nM in the test batch, and 5 μl of a compound according to the invention (dissolved in 25% DMSO in water) with a concentration of 10 μM in the test batch were incubated on a shaking machine for 40 minutes at room temperature in 96-well microtiter plates (polypropylene, Costar) and the incubated mixture was then filtered with suction on 96-well Unifilter plates with GF/B filters (Whatman) using a harvester (Robotic Harvester 9600, Brandel). The filter plates were preswollen for 40 minutes in buffer 3 (50 mM Tris, 0.5% PEI, pH 7.4) before the filtering step. The filter plates were washed three times with wash buffer (0.1 M NaCl with 0.05 $NaN_3$) after the filtering step in order to remove non-bound radioligand, and then dried in a drying cabinet at 55° C. After a cooling phase of 15 minutes, 35 μl of scintillator (Ultima Gold MV, Packard) were added per well and the radioactivity on the filters was then determined in a β-counter (Trilux Microbeta, Wallac).

The compounds corresponding to formula I, preferably corresponding to formula II, III, IV, V, VI or VII, showed a good inhibition or displacement of gabapentin in this assay as shown in Table 1. The compounds investigated therefore show an affinity to the hitherto unknown gabapentin-binding site in this one biochemical assay.

It can be expected that the compounds according to the invention display comparable pharmacological properties to gabapentin, e.g. as an agent against pain or epilepsy. This has been demonstrated by their analgesic action. Thus, the compounds according to the invention not only displace gabapentin from its binding site but also—like gabapentin—have a significant analgesic action.

TABLE 1

| | Gabapentin [%] inhibition |
|---|---|
| 1-(2-Chloro-benzyl)-2-(4-methyl-piperazin-1-ylmethyl)-cyclooctanol | 61 |
| 1-(4-Fluoro-benzyl)-2-(4-methyl-piperazin-1-ylmethyl)-cyclooctanol | 39 |
| 1-(3-Fluoro-benzyl)-2-(4-methyl-piperazin-1-ylmethyl)-cyclooctanol | 42 |
| 1-(2-Chloro-6-fluoro-benzyl)-2-(4-methyl-piperazin-1-ylmethyl)-cyclooctanol | 60 |
| 1-(2,4-Dichloro-benzyl)-2-(4-methyl-piperazin-1-ylmethyl)-cyclooctanol | 48 |
| 1-(2-Chloro-benzyl)-2-(4-methyl-piperazin-1-ylmethyl)-cycloheptanol | 74 |
| 1-(3-Fluoro-benzyl)-2-(4-methyl-piperazin-1-ylmethyl)-cycloheptanol | 44 |
| 1-(2-Chloro-6-fluoro-benzyl)-2-(4-methyl-piperzazin-1-ylmethyl)-cycloheptanol | 82 |
| 1-(2,4-Dichloro-benzyl)-2-(4-methyl-piperazin-1-ylmethyl)-cycloheptanol | 48 |
| 1-Benzyl-2-(4-methyl-piperazin-1-ylmethyl)-cyclododecanol | 56 |
| 2-(4-Methyl-piperazin-1-ylmethyl)-1-vinyl-cyclododecanol | 49 |
| 1-(3-Fluoro-benzyl)-2-(4-methyl-piperazin-1-ylmeethyl)-cyclododecanol | 45 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A pharmaceutical formulation comprising at least one N,N'-disubstituted piperazine compound corresponding to formula I

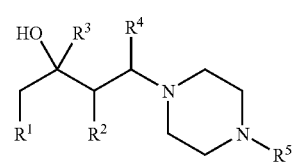

wherein $R^1$ and $R^2$ together form a $(CH_2)_n$ chain, wherein n represents an integer from 2-9;

$R^3$ represents a linear or branched, saturated or unsaturated aliphatic $C_{1-3}$ radical, a saturated or unsaturated cycloaliphatic $C_{5-6}$ radical, a phenyl radical, or a five- or six-membered heteroaryl radical, wherein the ring system of $R^3$ is optionally mono- or polysubstituted with halogen, an alkyl group, an alkoxy group or a trihalogenated alkyl group and is optionally bonded via a linear or branched, saturated or unsaturated aliphatic $C_{1-3}$ bridge; and $R^4$ represents hydrogen or a phenyl radical;

$R^5$ represents a linear or branched, saturated or unsaturated aliphatic $C_{1-3}$ radical or a phenyl radical optionally substituted with halogen or an alkoxy group;

or a salt thereof with a physiologically acceptable acid;

and optionally a physiologically acceptable auxiliary substance.

2. The pharmaceutical formulation of claim 1, wherein said compound is present in the form of a free base.

3. The pharmaceutical formulation of claim 1, wherein said compound is present in the form of a pure enantiomer or pure diastereoisomer.

4. The pharmaceutical formulation of claim 1, wherein said compound is present in the form of a mixture of stereoisomers.

5. The pharmaceutical formulation of claim 1, wherein said compound is present in the form of a racemic mixture.

6. The pharmaceutical formulation of claim 1, wherein $R^5$ represents a phenyl radical which is substituted by halogen or an alkoxy group.

7. A pharmaceutical formulation comprising at least one compound according to claim 1, wherein $R^1$ and $R^2$ together form a $(CH_2)_n$ chain, wherein n represents 3, 4, 5 or 9;

$R^3$ represents a vinyl radical, a cyclopentyl radical, a cyclohexyl radical, a cyclohexyl radical bonded via a methylene bridge, a thiophenyl radical an optionally mono- or polysubstituted phenyl radical, or an optionally mono- or polysubstituted phenyl radical bonded via a linear, saturated aliphatic $C_{1-3}$ bridge or an ethynyl bridge;

$R^4$ represents hydrogen or a phenyl radical; and $R^5$ represents a methyl group or an optionally substituted phenyl radical.

8. The pharmaceutical formulation of claim 7, wherein $R^3$ represents a cyclohexyl radical bonded via a methylene bridge or represents a phenyl radical which is mono- or polysubstituted by fluorine, chlorine, a methyl group, an isopropyl group, a methoxy group or a trifluoromethyl group or is bonded via a linear, saturated aliphatic $C_{1-3}$ bridge or an ethynyl bridge.

9. The pharmaceutical formulation of claim 7, wherein $R^5$ represents a phenyl radical which is substituted by chlorine or a methoxy group.

10. A pharmaceutical formulation comprising at least one compound according to claim 1, said compound corresponding to either

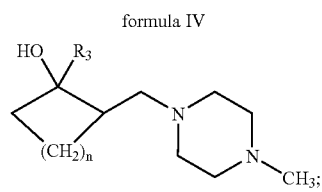

formula IV

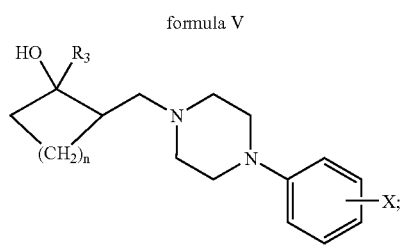

formula V

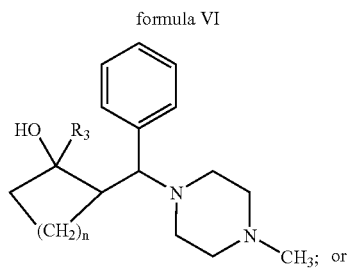

formula VI; or

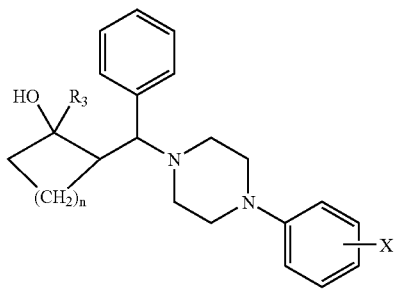

formula VII wherein n represents an integer from 2 to 9 and

X represents hydrogen, halogen or an alkoxy group.

11. A pharmaceutical formulation according to claim 10, wherein X represents chlorine or a methoxy group.

12. A pharmaceutical formulation according to claim 10, wherein the particular ring system of $R^3$ is mono- or polysubstituted by halogen, an alkyl group, an alkoxy group or a trihalogenated alkyl group or is bonded via a linear or branched, saturated or unsaturated aliphatic $C_{1-3}$ bridge.

13. A pharmaceutical formulation according to claim 10, wherein $R^3$ represents a vinyl radical, a cyclopentyl radical, a cyclohexyl radical, a cyclohexyl radical bonded via a methylene bridge, a thiophenyl radical, an optionally mono- or polysubstituted phenyl radical, or an optionally mono- or polysubstituted phenyl radical bonded via a linear, saturated aliphatic $C_{1-3}$ bridge or an ethynyl bridge.

14. A pharmaceutical formulation according to claim 13, wherein in $R^3$, the cyclohexyl radical is bonded via a methylene bridge or the phenyl radical is mono- or polysubstituted by fluorine, chlorine, a methyl group, an isopropyl group, a methoxy group or a trifluoromethyl group or is bonded via a linear, saturated aliphatic $C_{1-3}$ bridge or an ethynyl bridge.

15. A pharmaceutical formulation comprising at least one compound according to claim 1, wherein said compound is selected from the group consisting of:

2-(4-methyl-piperazin-1-ylmethyl)-1-phenyl-cyclohexanol;

1-benzyl-2-(4-methyl-piperazin-1-ylmethyl)-cyclohexanol;

1-(4-fluoro-3-methyl-phenyl)-2-(4-methyl-piperazin-1-ylmethyl)-cyclohexanol;

2-(4-methyl-piperazin-1-ylmethyl)-1-o-tolyl-cyclohexanol;

2-(4-methyl-piperazin-1-ylmethyl)-1-vinyl-cyclohexanol;

1-cyclopentyl-2-(4-methyl-piperazin-1-ylmethyl)-cyclohexanol;

2-(4-methyl-piperazin-1-ylmethyl)-1-m-tolyl-cyclohexanol;

2-(4-methyl-piperazin-1-ylmethyl)-bicyclohexyl-1-ol;

1-(4-fluoro-phenyl)-2-(4-methyl-piperazin-1-ylmethyl)-cyclohexanol;

2-(4-methyl-piperazin-1-ylmethyl)-1-phenethyl-cyclohexanol;

2-(4-methyl-piperazin-1-ylmethyl)-1-thiophen-2-yl-cyclohexanol;

1-(2,4-dichloro-phenyl)-2-(4-methyl-piperazin-1-ylmethyl)-cyclohexanol;

1-(3-methoxy-phenyl)-2-(4-methyl-piperazin-1-ylmethyl)-cyclohexanol;

2-(4-methyl-piperazin-1-ylmethyl)-1-(3-phenyl-propyl)-cyclohexanol;
2-(4-methyl-piperazin-1-ylmethyl)-1-p-tolyl-cyclohexanol;
1-(4-methoxy-phenyl)-2-(4-methyl-piperazin-1-ylmethyl)-cyclohexanol;
1-benzyl-2-(4-methyl-piperazin-1-ylmethyl)-cyclooctanol;
2-(4-methyl-piperazin-1-ylmethyl)-1-vinyl-cyclooctanol;
1-(4-tert-butyl-phenyl)-2-(4-methyl-piperazin-1-ylmethyl)-cyclooctanol;
1-cyclopentyl-2-(4-methyl-piperazin-1-ylmethyl)-cyclooctanol;
2-(4-methyl-piperazin-1-ylmethyl)-1-phenethyl-cyclooctanol;
2-(4-methyl-piperazin-1-ylmethyl)-1-phenylethynyl-cyclooctanol;
2-(4-methyl-piperazin-1-ylmethyl)-1-thiophen-2-yl-cyclooctanol;
1-(3-methoxy-phenyl)-2-(4-methyl-piperazin-1-ylmethyl)-cyclooctanol;
2-(4-methyl-piperazin-1-ylmethyl)-1-(3-phenyl-propyl)-cyclooctanol;
2-(4-methyl-piperazin-1-ylmethyl)-1-p-tolyl-cyclooctanol;
1-(4-methoxy-phenyl)-2-(4-methyl-piperazin-1-ylmethyl)-cyclooctanol;
2-(4-methyl-piperazin-1-ylmethyl)-1-phenyl-cycloheptanol;
1-(4-chloro-phenyl)-2-(4-methyl-piperazin-1-ylmethyl)-cycloheptanol;
1-benzyl-2-(4-methyl-piperazin-1-ylmethyl)-cycloheptanol;
1-(4-fluoro-3-methyl-phenyl)-2-(4-methyl-piperazin-1-ylmethyl)-cycloheptanol;
2-(4-methyl-piperazin-1-ylmethyl)-1-o-tolyl-cycloheptanol;
2-(4-methyl-piperazin-1-ylmethyl)-1-vinyl-cycloheptanol;
1-(4-tert-butyl-phenyl)-2-(4-methyl-piperazin-1-ylmethyl)-cycloheptanol;
1-cyclopentyl-2-(4-methyl-piperazin-1-ylmethyl)-cycloheptanol;
2-(4-methyl-piperazin-1-ylmethyl)-1-m-tolyl-cycloheptanol;
1-cyclohexylmethyl-2-(4-methyl-piperazin-1-ylmethyl)-cyclohexanol;
1-(5-fluoro-2-methoxy-phenyl)-2-(4-methyl-piperazin-1-ylmethyl)-cyclohexanol;
1-(3-fluoro-phenyl)-2-(4-methyl-piperazin-1-ylmethyl)-cyclohexanol;
1-(3-chloro-phenyl)-2-(4-methyl-piperazin-1-ylmethyl)-cyclohexanol;
1-(3,5-dichloro-phenyl)-2-(4-methyl-piperazin-1-ylmethyl)-cyclohexanol;
1-(2-chloro-benzyl)-2-(4-methyl-piperazin-1-ylmethyl)-cyclohexanol;
1-(4-fluoro-benzyl)-2-(4-methyl-piperazin-1-ylmethyl)-cyclohexanol;
1-(3-methoxy-benzyl)-2-(4-methyl-piperazin-1-ylmethyl)-cyclohexanol;
1-(4-chloro-3-trifluoromethyl-phenyl)-2-(4-methyl-piperazin-1-ylmethyl)-cyclohexanol;
1-(3-fluoro-benzyl)-2-(4-methyl-piperazin-1-ylmethyl)-cyclohexanol;
1-(2-methoxy-phenyl)-2-(4-methyl-piperazin-1-ylmethyl)-cyclohexanol;
1-(2-methyl-benzyl)-2-(4-methyl-piperazin-1-ylmethyl)-cyclohexanol;
1-(3-chloro-4-fluoro-phenyl)-2-(4-methyl-piperazin-1-ylmethyl)-cyclohexanol;
2-(4-methyl-piperazin-1-ylmethyl)-1-(3-trifluoromethyl-phenyl)-cyclohexanol;
1-(3-methyl-benzyl)-2-(4-methyl-piperazin-1-ylmethyl)-cyclohexanol;
1-(4-chloro-benzyl)-2-(4-methyl-piperazin-1-ylmethyl)-cyclohexanol;
1-(2,5-dimethyl-benzyl)-2-(4-methyl-piperazin-1-ylmethyl)-cyclohexanol;
1-(3-chloro-benzyl)-2-(4-methyl-piperazin-1-ylmethyl)-cyclohexanol;
1-(2,4-dichloro-benzyl)-2-(4-methyl-piperazin-1-ylmethyl)-cyclohexanol;
1-cyclohexylmethyl-2-(4-methyl-piperazin-1-ylmethyl)-cyclooctanol;
1-(5-fluoro-2-methoxy-phenyl)-2-(4-methyl-piperazin-1-ylmethyl)-cyclooctanol;
1-(2-chloro-benzyl)-2-(4-methyl-piperazin-1-ylmethyl)-cyclooctanol;
1-(4-fluoro-benzyl)-2-(4-methyl-piperazin-1-ylmethyl)-cyclooctanol;
1-(3-fluoro-benzyl)-2-(4-methyl-piperazin-1-ylmethyl)-cyclooctanol;
1-(2-methoxy-phenyl)-2-(4-methyl-piperazin-1-ylmethyl)-cyclooctanol;
1-(3-methyl-benzyl)-2-(4-methyl-piperazin-1-ylmethyl)-cyclooctanol;
1-(4-chloro-benzyl)-2-(4-methyl-piperazin-1-ylmethyl)-cyclooctanol;
1-(2-chloro-6-fluoro-benzyl)-2-(4-methyl-piperazin-1-ylmethyl)-cyclooctanol;
1-(2,5-dimethyl-benzyl)-2-(4-methyl-piperazin-1-ylmethyl)-cyclooctanol;
1-(3-chloro-benzyl)-2-(4-methyl-piperazin-1-ylmethyl)-cyclooctanol;
1-(2,4-dichloro-benzyl)-2-(4-methyl-piperazin-1-ylmethyl)-cyclooctanol;
1-cyclohexylmethyl-2-(4-methyl-piperazin-1-ylmethyl)-cycloheptanol;
1-(5-fluoro-2-methoxy-phenyl)-2-(4-methyl-piperazin-1-ylmethyl)-cycloheptanol;
1-(3-fluoro-phenyl)-2-(4-methyl-piperazin-1-ylmethyl)-cycloheptanol;
1-(3-chloro-phenyl)-2-(4-methyl-piperazin-1-ylmethyl)-cycloheptanol;
1-(3,5-dichloro-phenyl)-2-(4-methyl-piperazin-1-ylmethyl)-cycloheptanol;
1-(2-chloro-benzyl)-2-(4-methyl-piperazin-1-ylmethyl)-cycloheptanol;
1-(4-fluoro-benzyl)-2-(4-methyl-piperazin-1-ylmethyl)-cycloheptanol;
1-(3-methoxy-benzyl)-2-(4-methyl-piperazin-1-ylmethyl)-cycloheptanol;
1-(4-chloro-3-trifluoromethyl-phenyl)-2-(4-methyl-piperazin-1-ylmethyl)-cycloheptanol;
1-(3-fluoro-benzyl)-2-(4-methyl-piperazin-1-ylmethyl)-cycloheptanol;
1-(2-methoxy-phenyl)-2-(4-methyl-piperazin-1-ylmethyl)-cycloheptanol;
1-(2-methyl-benzyl)-2-(4-methyl-piperazin-1-ylmethyl)-cycloheptanol;
1-(3-chloro-4-fluoro-phenyl)-2-(4-methyl-piperazin-1-ylmethyl)-cycloheptanol;

2-(4-methyl-piperazin-1-ylmethyl)-1-(3-trifluoromethyl-phenyl)-cycloheptanol;
1-(3-methyl-benzyl)-2-(4-methyl-piperazin-1-ylmethyl)-cycloheptanol;
1-(4-chloro-benzyl)-2-(4-methyl-piperazin-1-ylmethyl)-cycloheptanol;
1-(2-chloro-6-fluoro-benzyl)-2-(4-methyl-piperazin-1-ylmethyl)-cycloheptanol;
1-(2,5-dimethyl-benzyl)-2-(4-methyl-piperazin-1-ylmethyl)-cycloheptanol;
1-(3-chloro-benzyl)-2-(4-methyl-piperazin-1-ylmethyl)-cycloheptanol;
1-(2,4-dichloro-benzyl)-2-(4-methyl-piperazin-1-ylmethyl)-cycloheptanol;
1-benzyl-2-(4-methyl-piperazin-1-ylmethyl)-cyclododecanol;
2-(4-methyl-piperazin-1-ylmethyl)-1-vinyl-cyclododecanol;
1-cyclopentyl-2-(4-methyl-piperazin-1-ylmethyl)-cyclododecanol;
2-(4-methyl-piperazin-1-ylmethyl)-1-phenethyl-cyclododecanol;
2-(4-methyl-piperazin-1-ylmethyl)-1-phenylethynyl-cyclododecanol;
2-(4-methyl-piperazin-1-ylmethyl)-1-thiophen-2-yl-cyclododecanol;
2-(4-methyl-piperazin-1-ylmethyl)-1-(3-phenyl-propyl)-cyclododecanol;
1-(5-fluoro-2-methoxy-phenyl)-2-(4-methyl-piperazin-1-ylmethyl)-cyclododecanol;
1-(2-chloro-benzyl)-2-(4-methyl-piperazin-1-ylmethyl)-cyclododecanol;
1-(4-fluoro-benzyl)-2-(4-methyl-piperazin-1-ylmethyl)-cyclododecanol;
1-(3-methoxy-benzyl)-2-(4-methyl-piperazin-1-ylmethyl)-cyclododecanol;
1-(3-fluoro-benzyl)-2-(4-methyl-piperazin-1-ylmethyl)-cyclododecanol;
1-(2-methoxy-phenyl)-2-(4-methyl-piperazin-1-ylmethyl)-cyclododecanol;
1-(2-methyl-benzyl)-2-(4-methyl-piperazin-1-ylmethyl)-cyclododecanol;
1-(3-methyl-benzyl)-2-(4-methyl-piperazin-1-ylmethyl)-cyclododecanol;
1-(4-chloro-benzyl)-2-(4-methyl-piperazin-1-ylmethyl)-cyclododecanol;
1-(2,5-dimethyl-benzyl)-2-(4-methyl-piperazin-1-ylmethyl)-cyclododecanol;
1-(3-chloro-benzyl)-2-(4-methyl-piperazin-1-ylmethyl)-cyclododecanol;
1-(2,4-dichloro-benzyl)-2-(4-methyl-piperazin-1-ylmethyl)-cyclododecanol;
2-[4-(3-chloro-phenyl)-piperazin-1-ylmethyl]-1-cyclohexylmethyl-cyclohexanol;
2-[4-(3-chloro-phenyl)-piperazin-1-ylmethyl]-1-(5-fluoro-2-methoxy-phenyl)-cyclohexanol;
2-[4-(3-chloro-phenyl)-piperazin-1-ylmethyl]-1-(3-fluoro-phenyl)-cyclohexanol;
1-(3-chloro-phenyl)-2-[4-(3-chloro-phenyl)-piperazin-1-ylmethyl]-cyclohexanol;
2-[4-(3-chloro-phenyl)-piperazin-1-ylmethyl]-1-(3,5-dichloro-phenyl)-cyclohexanol;
1-(2-chloro-benzyl)-2-[4-(3-chloro-phenyl)-piperazin-1-ylmethyl]-cyclohexanol;
2-[4-(3-chloro-phenyl)-piperazin-1-ylmethyl]-1-(4-fluoro-benzyl)-cyclohexanol;
2-[4-(3-chloro-phenyl)-piperazin-1-ylmethyl]-1-(4-chloro-3-trifluoromethylphenyl)-cyclohexanol;
2-[4-(3-chloro-phenyl)-piperazin-1-ylmethyl]-1-(3-fluoro-benzyl)-cyclohexanol;
2-[4-(3-chloro-phenyl)-piperazin-1-ylmethyl]-1-(2-methoxy-phenyl)-cyclohexanol;
1-(3-chloro-4-fluoro-phenyl)-2-[4-(3-chloro-phenyl)-piperazin-1-ylmethyl]-cyclohexanol;
2-[4-(3-chloro-phenyl)-piperazin-1-ylmethyl]-1-(3-trifluoromethyl-phenyl)-cyclohexanol;
2-[4-(3-chloro-phenyl)-piperazin-1-ylmethyl]-1-(3-methyl-benzyl)-cyclohexanol;
1-(4-chloro-benzyl)-2-[4-(3-chloro-phenyl)-piperazin-1-ylmethyl]-cyclohexanol;
1-(2-chloro-6-fluoro-benzyl)-2-[4-(3-chloro-phenyl)-piperazin-1-ylmethyl]-cyclohexanol;
2-[4-(3-chloro-phenyl)-piperazin-1-ylmethyl]-1-(2,5-dimethyl-benzyl)-cyclohexanol;
1-(3-chloro-benzyl)-2-[4-(3-chloro-phenyl)-piperazin-1-ylmethyl]-cyclohexanol;
2-[4-(2-chloro-phenyl)-piperazin-1-ylmethyl]-1-phenyl-cyclohexanol;
1-(4-chloro-phenyl)-2-[4-(2-chloro-phenyl)-piperazin-1-ylmethyl]-cyclohexanol;
1-benzyl-2-[4-(2-chloro-phenyl)-piperazin-1-ylmethyl]-cyclohexanol;
2-[4-(2-chloro-phenyl)-piperazin-1-ylmethyl]-1-(4-fluoro-3-methyl-phenyl)-cyclohexanol;
2-[4-(2-chloro-phenyl)-piperazin-1-ylmethyl]-1-o-tolyl-cyclohexanol;
2-[4-(2-chloro-phenyl)-piperazin-1-ylmethyl]-1-vinyl-cyclohexanol;
1-(4-tert-butyl-phenyl)-2-[4-(2-chloro-phenyl)-piperazin-1-ylmethyl]-cyclohexanol;
2-[4-(2-chloro-phenyl)-piperazin-1-ylmethyl]-1-cyclopentyl-cyclohexanol;
2-[4-(2-chloro-phenyl)-piperazin-1-ylmethyl]-1-m-tolyl-cyclohexanol;
2-[4-(2-chloro-phenyl)-piperazin-1-ylmethyl]-bicyclohexyl-1-ol;
2-[4-(2-chloro-phenyl)-piperazin-1-ylmethyl]-1-(4-fluoro-phenyl)-cyclohexanol;
2-[4-(2-chloro-phenyl)-piperazin-1-ylmethyl]-1-phenethyl-cyclohexanol;
2-[4-(2-chloro-phenyl)-piperazin-1-ylmethyl]-1-phenylethynyl-cyclohexanol;
2-[4-(2-chloro-phenyl)-piperazin-1-ylmethyl]-1-thiophen-2-yl-cyclohexanol;
2-[4-(2-chloro-phenyl)-piperazin-1-ylmethyl]-1-(3-methoxy-phenyl)-cyclohexanol;
2-[4-(2-chloro-phenyl)-piperazin-1-ylmethyl]-1-(3-phenyl-propyl)-cyclohexanol;
2-[4-(2-chloro-phenyl)-piperazin-1-ylmethyl]-1-p-tolyl-cyclohexanol;
2-[4-(2-chloro-phenyl)-piperazin-1-ylmethyl]-1-(4-methoxy-phenyl)-cyclohexanol;
2-[4-(2-chloro-phenyl)-piperazin-1-ylmethyl]-1-cyclohexylmethyl-cyclohexanol;
2-[4-(2-chloro-phenyl)-piperazin-1-ylmethyl]-1-(5-fluoro-2-methoxy-phenyl)-cyclohexanol;
1-(3-chloro-phenyl)-2-[4-(2-chloro-phenyl)-piperazin-1-ylmethyl]-cyclohexanol;
2-[4-(2-chloro-phenyl)-piperazin-1-ylmethyl]-1-(3,5-dichloro-phenyl)-cyclohexanol;
1-(2-chloro-benzyl)-2-[4-(2-chloro-phenyl)-piperazin-1-ylmethyl]-cyclohexanol;

2-[4-(2-chloro-phenyl)-piperazin-1-ylmethyl]-1-(4-fluoro-benzyl)-cyclohexanol;
2-[4-(2-chloro-phenyl)-piperazin-1-ylmethyl]-1-(3-methoxy-benzyl)-cyclohexanol;
2-[4-(2-chloro-phenyl)-piperazin-1-ylmethyl]-1-(4-chloro-3-trifluoromethyl-phenyl)-cyclohexanol;
2-[4-(2-chloro-phenyl)-piperazin-1-ylmethyl]-1-(3-fluoro-benzyl)-cyclohexanol;
2-[4-(2-chloro-phenyl)-piperazin-1-ylmethyl]-1-(2-methoxy-phenyl)-cyclohexanol;
2-[4-(2-chloro-phenyl)-piperazin-1-ylmethyl]-1-(2-methyl-benzyl)-cyclohexanol;
1-(3-chloro-4-fluoro-phenyl)-2-[4-(2-chloro-phenyl)-piperazin-1-ylmethyl]-cyclohexanol;
2-[4-(2-chloro-phenyl)-piperazin-1-ylmethyl]-1-(3-trifluoromethyl-phenyl)-cyclohexanol;
2-[4-(2-chloro-phenyl)-piperazin-1-ylmethyl]-1-(3-methyl-benzyl)-cyclohexanol;
1-(4-chloro-benzyl)-2-[4-(2-chloro-phenyl)-piperazin-1-ylmethyl]-cyclohexanol;
1-(2-chloro-6-fluoro-benzyl)-2-[4-(2-chloro-phenyl)-piperazin-1-ylmethyl]-cyclohexanol;
2-[4-(2-chloro-phenyl)-piperazin-1-ylmethyl]-1-(2,5-dimethyl-benzyl)-cyclohexanol;
1-(3-chloro-benzyl)-2-[4-(2-chloro-phenyl)-piperazin-1-ylmethyl]-cyclohexanol;
2-[4-(2-chloro-phenyl)-piperazin-1-ylmethyl]-1-(2,4-dichloro-benzyl)-cyclohexanol;
2-[4-(2-methoxy-phenyl)-piperazin-1-ylmethyl]-1-phenyl-cyclohexanol;
1-(4-chloro-phenyl)-2-[4-(2-methoxy-phenyl)-piperazin-1-ylmethyl]-cyclohexanol;
1-benzyl-2-[4-(2-methoxy-phenyl)-piperazin-1-ylmethyl]-cyclohexanol;
1-(4-fluoro-3-methyl-phenyl)-2-[4-(2-methoxy-phenyl)-piperazin-1-ylmethyl]-cyclohexanol;
2-[4-(2-methoxy-phenyl)-piperazin-1-ylmethyl]-1-o-tolyl-cyclohexanol;
2-[4-(2-methoxy-phenyl)-piperazin-1-ylmethyl]-1-vinyl-cyclohexanol;
1-(4-tert-butyl-phenyl)-2-[4-(2-methoxy-phenyl)-piperazin-1-ylmethyl]-cyclohexanol;
1-cyclopentyl-2-[4-(2-methoxy-phenyl)-piperazin-1-ylmethyl]-cyclohexanol;
2-[4-(2-methoxy-phenyl)-piperazin-1-ylmethyl]-1-m-tolyl-cyclohexanol;
2-[4-(2-methoxy-phenyl)-piperazin-1-ylmethyl]-bicyclohexyl-1-ol;
1-(4-fluoro-phenyl)-2-[4-(2-methoxy-phenyl)-piperazin-1-ylmethyl]-cyclohexanol;
2-[4-(2-methoxy-phenyl)-piperazin-1-ylmethyl]-1-phenethyl-cyclohexanol;
2-[4-(2-methoxy-phenyl)-piperazin-1-ylmethyl]-1-phenylethynyl-cyclohexanol;
2-[4-(2-methoxy-phenyl)-piperazin-1-ylmethyl]-1-thiophen-2-yl-cyclohexanol;
1-(3-methoxy-phenyl)-2-[4-(2-methoxy-phenyl)-piperazin-1-ylmethyl]-cyclohexanol;
2-[4-(2-methoxy-phenyl)-piperazin-1-ylmethyl]-1-(3-phenyl-propyl)-cyclohexanol;
1-(2,3-dichloro-phenyl)-2-[4-(2-methoxy-phenyl)-piperazin-1-ylmethyl]-cyclohexanol;
2-[4-(2-methoxy-phenyl)-piperazin-1-ylmethyl]-1-p-tolyl-cyclohexanol;
1-(4-methoxy-phenyl)-2-[4-(2-methoxy-phenyl)-piperazin-1-ylmethyl]-cyclohexanol;
1-cyclohexylmethyl-2-[4-(2-methoxy-phenyl)-piperazin-1-ylmethyl]-cyclohexanol;
1-(5-fluoro-2-methoxy-phenyl)-2-[4-(2-methoxy-phenyl)-piperazin-1-ylmethyl]-cyclohexanol;
1-(3-fluoro-phenyl)-2-[4-(2-methoxy-phenyl)-piperazin-1-ylmethyl]-cyclohexanol;
1-(3-chloro-phenyl)-2-[4-(2-methoxy-phenyl)-piperazin-1-ylmethyl]-cyclohexanol;
1-(3,5-dichloro-phenyl)-2-[4-(2-methoxy-phenyl)-piperazin-1-ylmethyl]-cyclohexanol;
1-(2-chloro-benzyl)-2-[4-(2-methoxy-phenyl)-piperazin-1-ylmethyl]-cyclohexanol;
1-(4-fluoro-benzyl)-2-[4-(2-methoxy-phenyl)-piperazin-1-ylmethyl]-cyclohexanol;
1-(3-methoxy-benzyl)-2-[4-(2-methoxy-phenyl)-piperazin-1-ylmethyl]-cyclohexanol;
1-(4-chloro-3-trifluoromethyl-phenyl)-2-[4-(2-methoxy-phenyl)-piperazin-1-ylmethyl]-cyclohexanol;
1-(3-fluoro-benzyl)-2-[4-(2-methoxy-phenyl)-piperazin-1-ylmethyl]-cyclohexanol;
1-(2-methoxy-phenyl)-2-[4-(2-methoxy-phenyl)-piperazin-1-ylmethyl]-cyclohexanol;
2-[4-(2-methoxy-phenyl)-piperazin-1-ylmethyl]-1-(2-methyl-benzyl)-cyclohexanol;
1-(3-chloro-4-fluoro-phenyl)-2-[4-(2-methoxy-phenyl)-piperazin-1-ylmethyl]-cyclohexanol;
2-[4-(2-methoxy-phenyl)-piperazin-1-ylmethyl]-1-(3-trifluoromethyl-phenyl)-cyclohexanol;
2-[4-(2-methoxy-phenyl)-piperazin-1-ylmethyl]-1-(3-methyl-benzyl)-cyclohexanol;
1-(4-chloro-benzyl)-2-[4-(2-methoxy-phenyl)-piperazin-1-ylmethyl]-cyclohexanol;
1-(2-chloro-6-fluoro-benzyl)-2-[4-(2-methoxy-phenyl)-piperazin-1-ylmethyl]-cyclohexanol;
1-(2,5-dimethyl-benzyl)-2-[4-(2-methoxy-phenyl)-piperazin-1-ylmethyl]-cyclohexanol;
1-(3-chloro-benzyl)-2-[4-(2-methoxy-phenyl)-piperazin-1-ylmethyl]-cyclohexanol;
1-(2,4-dichloro-benzyl)-2-[4-(2-methoxy-phenyl)-piperazin-1-ylmethyl]-cyclohexanol;
1-benzyl-2-[4-(2-methoxy-phenyl)-piperazin-1-ylmethyl]-cyclododecanol;
2-[4-(2-methoxy-phenyl)-piperazin-1-ylmethyl]-1-vinyl-cyclododecanol;
1-phenethyl-2-[phenyl-(4-phenyl-piperazin-1-yl)-methyl]-cyclohexanol;
1-benzyl-2-[(4-methyl-piperazin-1-yl)-phenyl-methyl]-cyclohexanol;
1-benzyl-2-[phenyl-(4-phenyl-piperazin-1-yl)-methyl]-cyclohexanol;
2-[(4-methyl-piperazin-1-yl)-phenyl-methyl]-1-phenethyl-cyclohexanol; and
2-[4-(2-methoxy-phenyl)-piperazin-1-ylmethyl]-1-phenethyl-cyclododecanol.

* * * * *